(12) United States Patent
Cryder et al.

(10) Patent No.: US 10,092,283 B2
(45) Date of Patent: Oct. 9, 2018

(54) DEVICES AND SYSTEMS FOR SURGICAL RETRACTION

(71) Applicant: GLOBUS MEDICAL, INC., Audubon, PA (US)

(72) Inventors: Joel Cryder, Chalfont, PA (US); Edward Karpowicz, Sewell, NJ (US)

(73) Assignee: Globus Medical Inc, Audubon, PA (US)

( * ) Notice: Subject to any disclaimer, the term of this patent is extended or adjusted under 35 U.S.C. 154(b) by 0 days.

(21) Appl. No.: 15/615,089

(22) Filed: Jun. 6, 2017

(65) Prior Publication Data

US 2017/0265850 A1    Sep. 21, 2017

Related U.S. Application Data

(62) Division of application No. 14/828,695, filed on Aug. 18, 2015, now Pat. No. 9,700,293.

(51) Int. Cl.
| | | |
|---|---|---|
| *A61B 17/02* | (2006.01) | |
| *A61B 17/70* | (2006.01) | |
| *A61B 17/86* | (2006.01) | |

(52) U.S. Cl.
CPC ........ *A61B 17/025* (2013.01); *A61B 17/0206* (2013.01); *A61B 17/708* (2013.01); *A61B 17/86* (2013.01); *A61B 2017/0256* (2013.01)

(58) Field of Classification Search
CPC ... A61B 17/02; A61B 17/0218; A61B 17/025; A61B 17/0206; A61B 17/7074; A61B 17/7077; A61B 17/708; A61B 17/7083; A61B 17/7085; A61B 2017/0256; A61B 2017/0262; A61B 2017/0268
See application file for complete search history.

(56) References Cited

U.S. PATENT DOCUMENTS

| | | | |
|---|---|---|---|
| 8,636,655 B1* | 1/2014 | Childs | A61B 17/0206 600/219 |
| 9,044,280 B1* | 6/2015 | Arambula | A61B 17/0206 |
| 9,795,417 B2* | 10/2017 | Beger | A61B 17/7037 |
| 2007/0270842 A1* | 11/2007 | Bankoski | A61B 17/00234 606/86 A |
| 2010/0268284 A1 | 10/2010 | Bankoski et al. | |
| 2011/0130793 A1* | 6/2011 | Woolley | A61B 17/0206 606/279 |
| 2012/0245431 A1 | 9/2012 | Baudouin et al. | |

(Continued)

FOREIGN PATENT DOCUMENTS

JP    2014050714 A    3/2014

*Primary Examiner* — Lynnsy Summitt

(57) ABSTRACT

Retractor blade assemblies, retractors, kits, and methods of using the same. The retractor blade assembly may include a retractor blade, a pedicle screw, and a shim that connects the pedicle screw to the retractor blade. The retractor blade may have a proximal end configured to engage a retractor body and a distal end configured to retract soft tissue. The pedicle screw may have a head portion removably connected to the distal end of the retractor blade and a shaft portion configured to engage the pedicle of a vertebra. The shim couples the pedicle screw to the retractor blade. For example, the shim may include an extension portion configured to engage the retractor blade and a connection portion configured to receive and temporarily lock the pedicle screw to the retractor blade.

17 Claims, 15 Drawing Sheets

(56) References Cited

U.S. PATENT DOCUMENTS

| | | | |
|---|---|---|---|
| 2012/0296171 A1* | 11/2012 | Lovell | A61B 17/0206 600/213 |
| 2014/0018633 A1 | 1/2014 | Woolley et al. | |
| 2014/0066718 A1 | 3/2014 | Fiechter et al. | |
| 2014/0114137 A1 | 4/2014 | Reglos et al. | |
| 2015/0164569 A1* | 6/2015 | Reitblat | A61B 17/7077 606/279 |

* cited by examiner

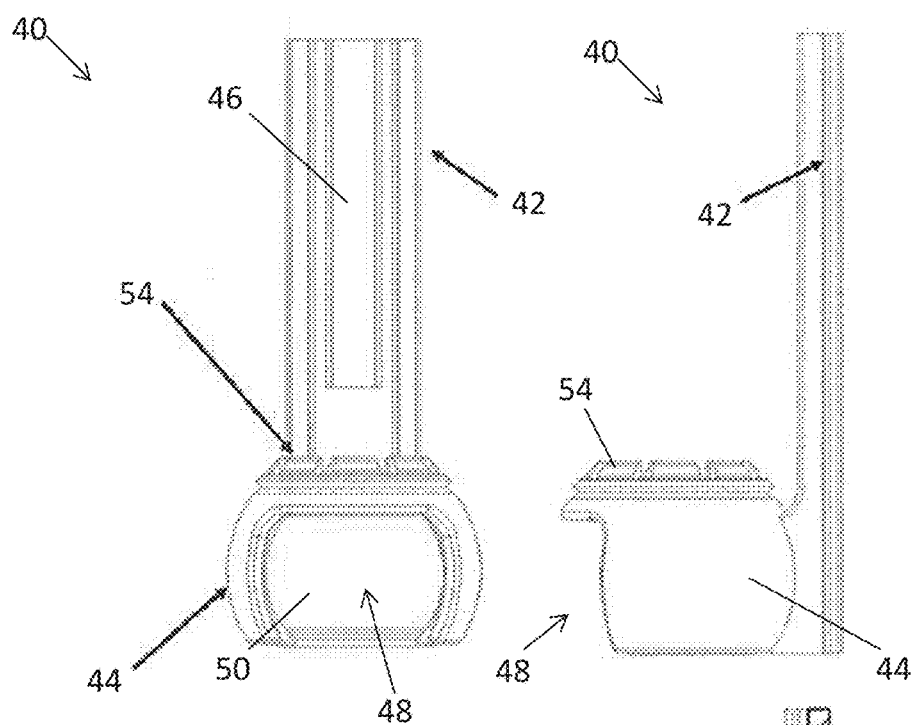
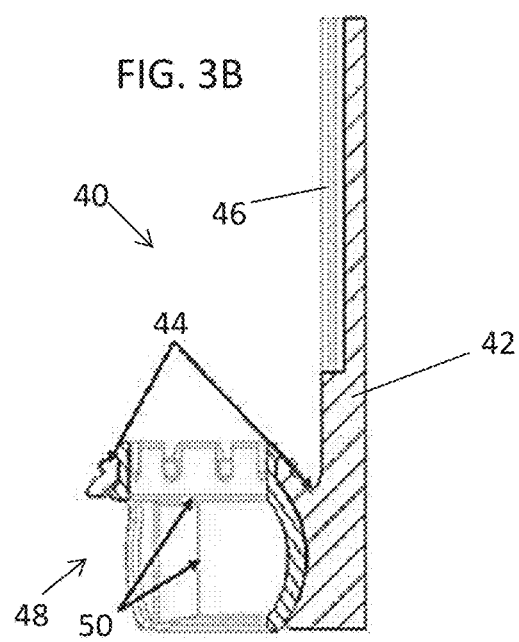
FIG. 3A   FIG. 3B
FIG. 3C

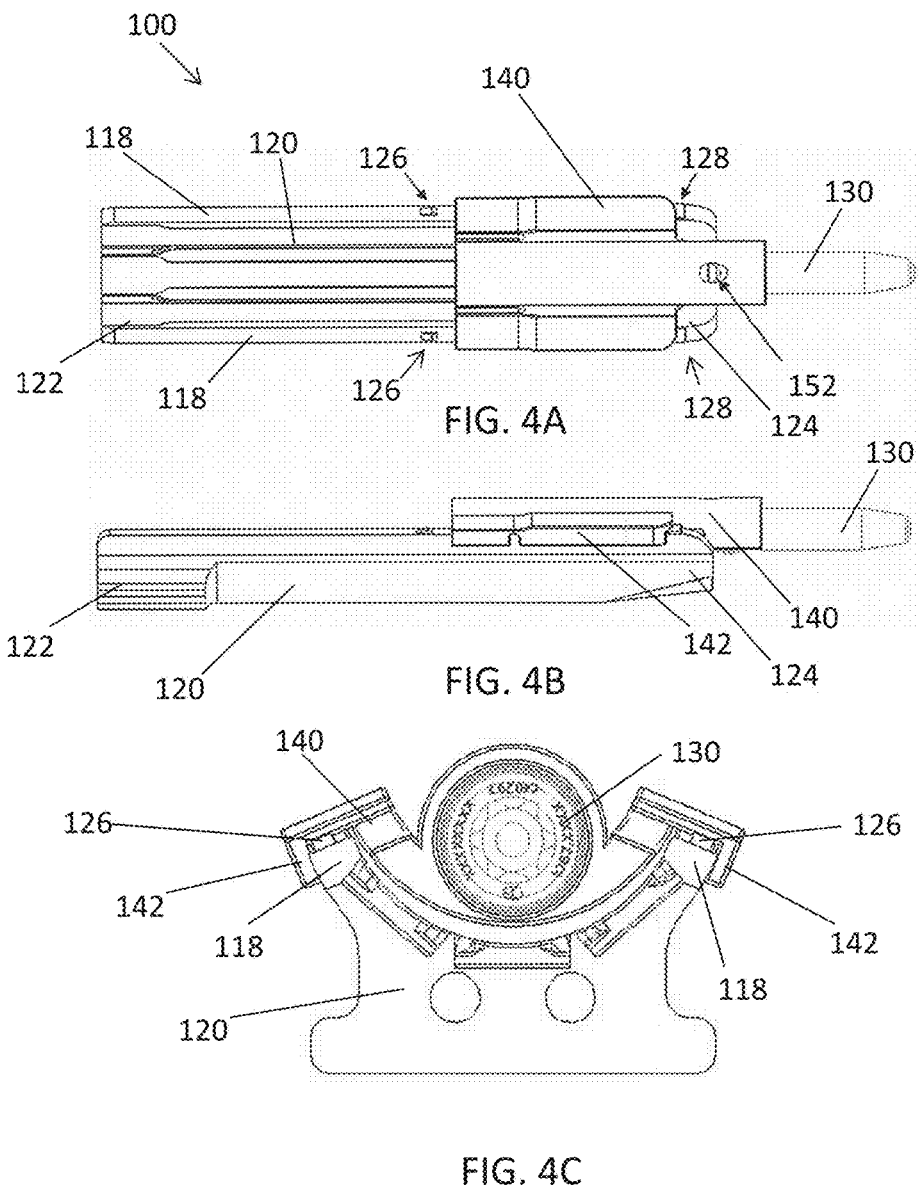

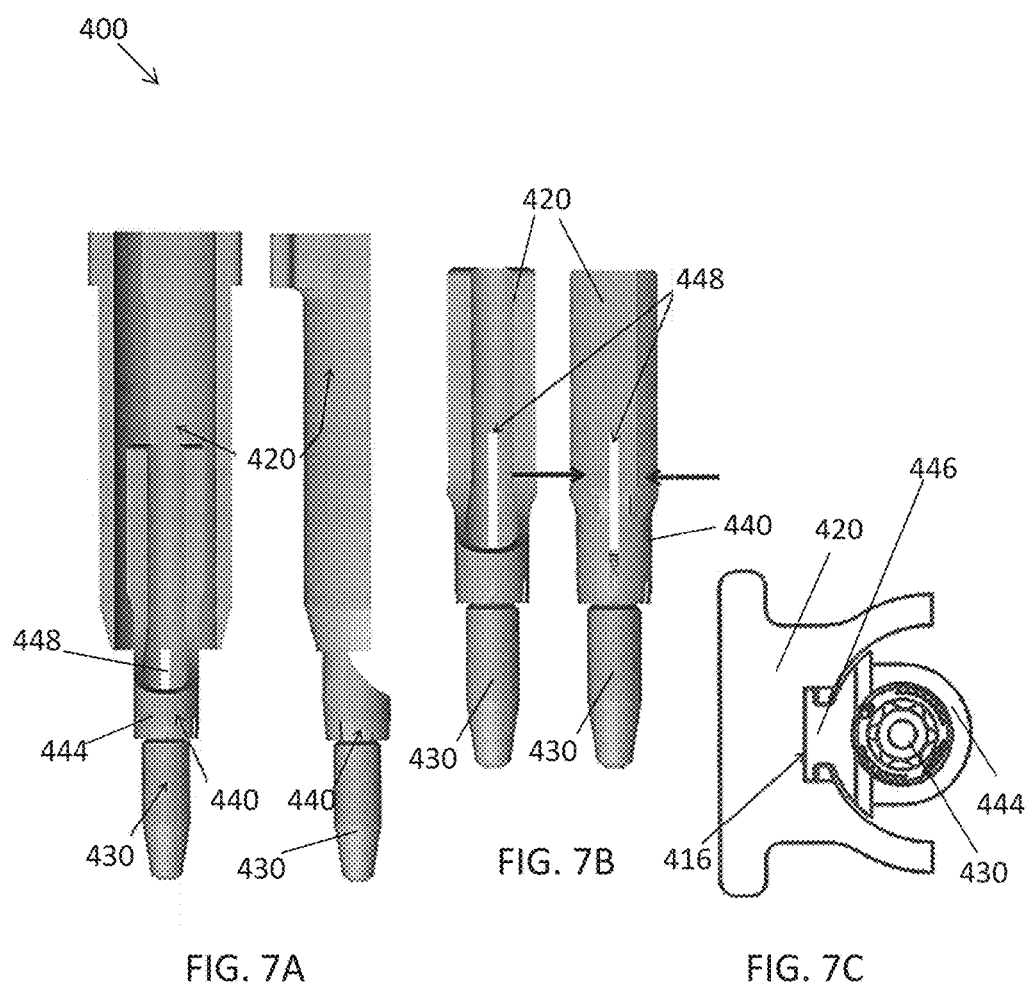

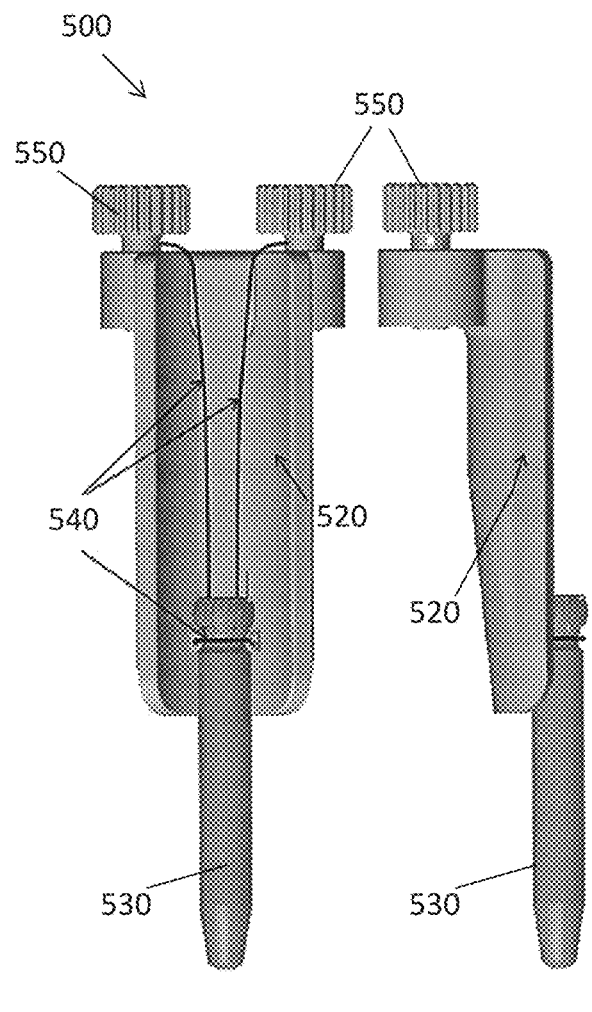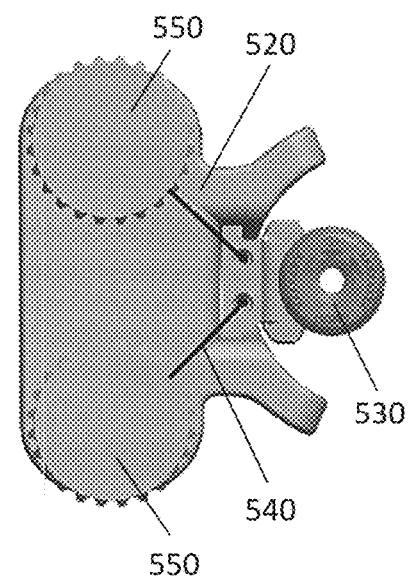
FIG. 8A    FIG. 8B    FIG. 8C

DEVICES AND SYSTEMS FOR SURGICAL RETRACTION

CROSS REFERENCE TO RELATED APPLICATIONS

The present application is a divisional application of U.S. patent application Ser. No. 14/828,695 filed on Aug. 18, 2015, which is incorporated in its entirety herein.

FIELD OF THE INVENTION

The present disclosure generally relates to devices and systems for performing pedicle-based surgical retraction and/or distraction and methods of use thereof.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated through a surgical procedure that may include, for example, immobilizing a portion of the spine. These treatments may involve, for example, replacing a damaged disc with an intervertebral implant and/or securing the adjacent vertebrae, for example, with a combination of screws and rods. For correction of a collapsed disc causing impingement of one or more nerve roots, for example, the disc space may be restored back to or near its original height and the collapsed disc may be replaced with a device and/or bone graft material.

In order to perform these procedures, a surgical opening is created, and a device such as a retractor may be used to enlarge the opening and facilitate access to the surgical site. The retractor may typically include one or more blades that can be adjusted to establish, provide, and/or maintain an appropriate opening that minimizes trauma to surrounding tissue. A distractor may also be used to distract the disc space, for example, by placing a portion of the distractor between vertebral bodies or by using adjacent level pedicle screws.

By using a pedicle-based retraction system, the retractor can perform the functions of both a retractor and a distractor. For example, the blades may provide for soft tissue retraction, and the pedicle screws may be configured to simultaneously facilitate distraction of the disc space. There is a need, however, for improved retractors which provide pedicle-based distraction and soft tissue retraction. For example, pedicle-based retractors require a secure connection between the blade and the pedicle screw. It is also desirable to have a mechanism to attach the blades to the screws after the screws have already been affixed to bone. Preferably, there is a minimal amount of tissue disruption when connecting the blades to the screws intra-operatively.

SUMMARY OF THE INVENTION

To meet this and other needs, devices, systems, and methods for performing pedicle-based surgical retraction are provided. In particular, the pedicle-based retractors are provided with specially designed connections between the pedicle screw and blade, which create a secure reversible connection between the pedicle screw and the retractor blade. After the screw is implanted in the bone, the blade may be attached to the screw in a manner to minimize the amount of tissue disruption at the surgical site.

According to one embodiment, a retractor blade assembly includes a retractor blade, a screw, and a shim which connects the screw to the retractor blade. The retractor blade may have a proximal end configured to engage a retractor body and a distal end configured to retract soft tissue. The screw may have a head portion removably connectable to the distal end of the retractor blade and a shaft portion configured to engage bone. The shim may have an extension portion configured to engage the retractor blade and a connection portion configured to receive at least a portion of the screw. The connection portion may be movable from an unlocked position to a locked position for retaining the screw within the shim.

According to another embodiment, a retractor assembly includes a retractor body, at least one retractor blade, at least one pedicle screw, and at least one shim that connects the pedicle screw to the retractor blade. The retractor blade may have a proximal end configured to engage the retractor body and a distal end configured to retract soft tissue. The pedicle screw may have a head portion removably connectable to the distal end of the retractor blade and a shaft portion configured to engage bone. The shim may have an extension portion, an outer spherical portion, and an inner spherical portion rotatably received within the outer spherical portion. The extension portion may be configured to engage the retractor blade and the inner spherical portion may be configured to receive the head portion of the pedicle screw. The inner spherical portion rotates from an unlocked position to a locked position for retaining the head portion of the pedicle screw within the shim.

The retractor blade assembly and/or the retractor assembly may include one or more of the following attributes: the extension portion may include at least one rail configured to slidably engage at least one corresponding rail on the retractor blade; the extension portion may include at least one edge configured to surround one or both end portions of the retractor blade; the retractor blade may include a generally curved inner portion having one or more grooves defined along at least a portion of the at least one retractor blade, the one or more grooves configured to slidably engage one or more corresponding tongues of the extension portion of the at least one shim; the shim may include an elongated slot extending longitudinally along a length of the shim; the connection portion may be configured to rotate relative to the retractor blade; the connection portion may include at least a partial ring configured to at least partially surround the head portion of the screw; a top portion of the inner spherical portion may extend through an opening in the outer spherical portion, and the top portion may be configured to be engaged by a driver in order to rotate the inner spherical portion from the unlocked position to the locked position; the screw may be side-loaded into the shim; the outer spherical portion and the inner spherical portion may each include an opening that, when aligned, allow the pedicle screw to be side-loaded into the shim; the pedicle screw may be configured to polyaxially rotate in the shim; one or more locks may be positioned along one or both outer edges of the retractor blade to prevent the shim from sliding off the retractor blade; and the driver may include at least one track configured to engage the at least one rail on the extension portion of the shim.

According to yet another embodiment, a method of retracting and distracting a disc space between first and second vertebrae may include: (a) connecting a driver to a first shim; (b) attaching a first pedicle screw to the first shim by side loading the first pedicle screw into the first shim and locking the first pedicle screw to the first shim; (c) attaching the first pedicle screw to a pedicle of the first vertebra; (d) sliding a first retractor blade having a proximal portion and a distal portion down the driver and onto the first shim such that the distal portion of the first retractor blade connects to the first shim; (e) removing the driver; and (f) connecting a retractor body to the proximal portion of the first retractor blade. In addition, the method may optionally include: (g) connecting the driver to a second shim; (h) attaching a second pedicle screw to the second shim by side loading the second pedicle screw into the second shim and locking the second pedicle screw to the second shim; (i) attaching the second pedicle screw to a pedicle of the second vertebra; (j) sliding a second retractor blade having a proximal portion and a distal portion down the driver and onto the second shim such that the distal portion of the second retractor blade connects to the second shim; (k) removing the driver; (l) connecting the retractor body to the proximal portion of the second retractor blade; and (m) retracting and distracting the disc space using the first and second retractor blades and the first and second pedicle screws, respectively.

According to yet another embodiment, a kit may include a plurality shims, blades, and/or screws of different sizes and different configurations. The kit may further include one or more retractor bodies and attachment mechanisms, such as surgical arms, table arms, or the like. In addition, the kit may include one or more devices suitable for installing and/or removing the retractor blade assemblies described herein, such as insertion devices or drivers; one or more removal devices or drivers; and other tools and devices, which may be suitable for surgery.

BRIEF DESCRIPTION OF THE DRAWINGS

The present embodiments will become more fully understood from the detailed description and the accompanying drawings, wherein:

FIGS. 4A-4C show attachment of a retractor blade member to a pedicle screw according to another embodiment;

FIGS. 7A-7C illustrate yet another attachment mechanism between a pedicle screw and retractor blade; and FIGS. 8A-8C show attachment of a retractor blade member to a pedicle screw according to another embodiment.

DETAILED DESCRIPTION

Figure 1:
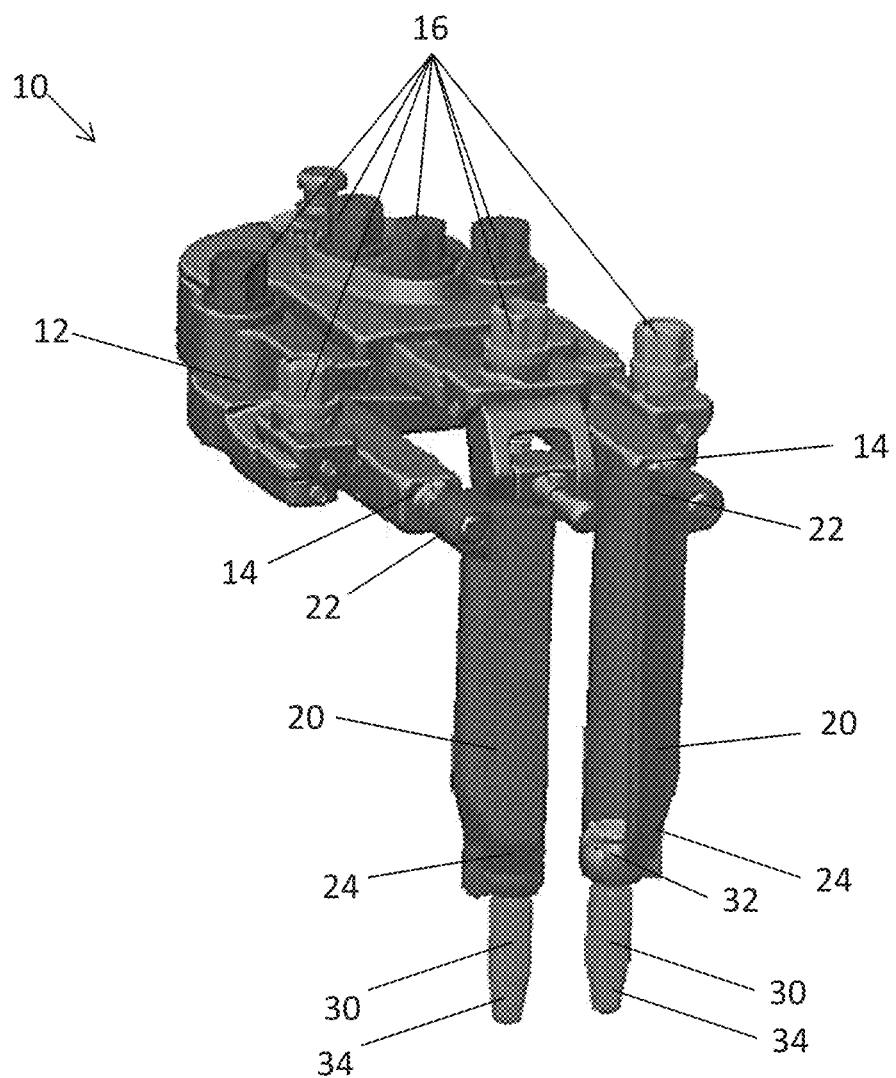
FIG. 1 illustrates a perspective view of a retractor assembly according to one embodiment.

Embodiments of the disclosure are generally directed to devices, systems, kits, and methods for retraction and/or distraction using a pedicle-based retraction system. Specifically, the pedicle-based retractors include secure and reversible connections between the pedicle screw and retractor blade. The retractor blade may be attached to the screw before or after the screw has been implanted in the bone. When attached intra-operatively, the attachment mechanism may minimize the amount of tissue disruption at the surgical site.

In a spinal fusion procedure, a damaged spinal disc may be removed and replaced with an intervertebral implant (e.g., a cage, spacer, vertebral body replacement, bone graft material, or other prosthetic). The adjacent vertebrae may be stabilized, for example, with a combination of screws and rods. The operation may be performed in an open procedure, semi-open procedure, percutaneous, or in a minimally invasive surgical (MIS) procedure. As part of the procedure, a retractor may be used to establish, enlarge, manipulate, and/or maintain a surgical opening, thereby facilitating the passage of the various implant devices and related tools. In some instances, different retractors may be used for different surgical approaches (e.g., anterior, posterior, transforaminal, lateral), due to the varying anatomical features unique to each approach. The retractor blades may be used to hold back soft tissue and muscle, and precise angling of the retractor's blades may depend at least in part on various factors, including the particular patient's anatomy and surgeon's preference.

Overall, retractor systems disclosed herein may advantageously provide a screw-based retraction and distraction, resulting in more precise tissue retraction and distraction of adjacent bones. In particular, a pedicle-based retraction system may include one or more retractor blades temporarily affixed to one or more pedicle screws each configured to engage a pedicle of a vertebra. Once attached to a retractor body, the retractor blades and attached pedicles may retract soft tissue and/or muscle and distract the disc space. Although described herein with regards to specific pedicle-based blade designs, those skilled in the art may appreciate that the blades described herein may be used in any suitable retractor design.

As used herein, the terms "proximal" and "distal" are utilized generally with reference to a user (e.g., a surgeon). When used with reference to the retractor assembly, described further herein, the terms "lateral" and "medial" refer generally to the ends and the middle position, respectively. For example, a retractor arm traveling in a lateral direction may be traveling from a middle portion outwardly, and a retractor arm traveling in a medial direction may be traveling from an end portion towards the middle. These and other directional terms such as "top" and "bottom" and the like may be used herein for descriptive purposes and do not limit the orientation(s) in which the devices may be used.

Some embodiments may include a two-bladed retractor. The retraction may be controlled medially and laterally, for example. Each blade may also have a towing or pivoting capability. Although a two blade design is exemplified, it is understood that the retractor may encompass three or more blades, four or more blades, or the like in order to provide retraction in the medial, lateral, cephalad, caudal, or other orientations as may be desired.

The retractor system may include a variety of sub-components dimensioned to allow for retraction of soft tissue and/or muscle in order to establish an operative corridor through a patient's skin to a surgical target site as well as a screw-based component to allow for distraction of adjacent bones. By way of example, the surgical target site may be an intervertebral disc space situated between two adjacent vertebrae. Although particularly suited for use in a transforaminal lumbar interbody fusion (TLIF), it will be readily appreciated by those skilled in the art that the retractor system may be employed in any number of suitable orthopedic approaches and procedures, including but not limited to, anterior, posterior, lateral, anterolateral, or posterolateral approaches to the lumbar spine, cervical spine, or thoracic spine, as well as any non-spine application, such as treatment of bone fractures and the like.

Turning now to the drawing, where like reference numerals refer to like elements, FIG. 1 illustrates a retractor system 10. The retractor system 10 includes a frame or base 12 that is attachable to an arm and/or supporting structure (not shown). For example, the base 12 may be directly or indirectly attachable to a table, a rack, a cart, or the like. In one embodiment, the base 12 is configured to be attached to a surgical arm, such as a universal arm, which includes enough joints to provide a desired number of degrees of freedom to easily adjust the base 12 over an incision in a patient. Preferably, the base 12 is configured to be positioned in a substantially stationary position over the surgical access site.

Broadly, the base 12 provides a scaffold to hold the various components together and one or more mechanisms for operating the retraction and/or distraction. In particular, the base 12 provides a mechanism to expand the operative corridor by moving the retractor blades 20 toward or away from one another. The base 12 may include one or more arms or posts 14 configured to receive or attach to one or more blades 20 thereto. Each post 14 is configured to enable the retractor blades 20 to retract nearby soft tissue and/or distract a bone segment. The base 12 includes one or more knobs 16 configured to operate the retractor 10. For example, the knobs 16 may provide for movement of posts 14, thereby providing for movement of the blades 20. Each of the respective knobs 16 may provide for independent movement of each respective blade 20 including lateral movement, medial movement, pivoting or towing or the blades 20, or the like as will be recognized by one of ordinary skill in the art. Although one type of retractor 10 is exemplified herein, it is understood that any suitable retractors known in the art may be used. Further detail of such devices may be found, for example, in U.S. Pat. Nos. 8,852,090; 8,932,215; 8,968,363; and 8,992,425, which are incorporated by reference herein in their entireties for all purposes.

One or more blades 20 are removably coupled to the base 10. The position of each retractor blade 20 can be changed independent from the other retractor blades 20, which allows a great amount of flexibility to the surgeon to explore an operating field. Furthermore, the position of each retractor blade 20 can be changed without changing the position of the base 10. Thus, the base 10 may remain in a substantially stationary and fixed position over the incision. In this regard, a change in the operating field can be obtained by changing the position of the blades 20.

In general, each retractor blade 20 has a first, proximal end portion 22 configured to engage with the base 12, for example, having an opening to receive post 14 and a second, distal end portion 24 configured to connect with a screw member 30. Each blade also includes an inner face, an outer face, and a longitudinal axis running the length of the blade 20 from the proximal end 22 to the opposite distal end 24. Different blade geometries may be used based on the patient anatomy and surgeon preference. For example, the blades 20 may be provided with a convexity at the proximal end 22 to cup under tissue and muscle to prevent the blades 20 and retractor from floating upward. In one embodiment, the retractor blades 20 have a curved or partial cylindrical shape, such that when blades 20 are aligned adjacent one another, a cylinder, channel, cannula, or the like is created therebetween. The size of the retractor blades 20 may dependent on the type of surgical procedure. The type, size, and shape of the surgical retractor blades 20 can be mixed together as well as changed or renewed during a surgical procedure.

The screw member 30 is configured to be removably attached to the retractor blade 20 as described in the various embodiment provided herein. The screw member 30 may include a head portion 32 (e.g., an enlarged head 32) at a proximal end configured to engage the retractor blade 20 and a shank or bone engagement portion 34 configured to engage bone, for example, having a taper at a distal end. The screw member 30 may be centrally cannulated along a longitudinal length from the proximal end to the distal end of the screw member 30, for example, such that the screw member 30 may be guided over a k-wire or the like. The screw member 30 may be in the form of a pedicle screw 30 having a threaded portion configured to engage the pedicle in a vertebral body. The head portion 32 may also be threaded or non-threaded. The pedicle screw 30 may be configured to provide uni-planar, bi-planar, or poly-axial orientation of the shank, for example. In the alternative, the screw member 30 may include any fixation members, such as nails, spikes, shims, or the like, which are known in the art.

With reference on FIGS. 2A-2D, a system and method for attaching a pedicle screw member 30 to a blade 20 is provided. In particular, a shim or screw mount 40 connects the pedicle screw member 30 to the blade 20. The shim or screw mount 40 includes an extension portion 42 and a head portion 44. The extension portion 42 may include a track 46, for example, in the form of one or more recesses and/or protrusions extending along a longitudinal length of the extension portion 42. The track 46 is configured to slidably engage and mate with a corresponding track portion 62 on a driver 60. The head portion 44 of the screw mount 40 may be sized and configured to receive the head 32 from the screw member 30. In particular, the head portion 44 may define an opening or aperture 48 configured to allow for side-loading of the screw member 30. The head portion 44 may house an internal sphere 50 within. The internal sphere 50 may be sized and configured to rotationally reside within the head portion 44 of the screw mount 40. The internal sphere 50 may have an opening or aperture corresponding to aperture 48 in the head portion 44, when in an unlocked position, such that the screw member 30 may be side loaded into the screw mount 40. The internal sphere 50 may be rotated by driver 60 such that the aperture 48 of the head portion 44 is substantially blocked, thereby locking the screw member 30 within the head portion 44 of the screw mount 40 in a locked position.

The driver 60 may include a distal portion configured to engage the screw mount 40 and a proximal portion configured to engage a handle (not shown) or other instrumentation to be manipulated by a user (e.g., a surgeon). For example, a quick connect handle may be attached to the driver 60. The driver 60 may include an elongated outer shaft 66 having an inner shaft 68 received longitudinally therethrough. The inner shaft 68 may also be cannulated along its length, for example, to be guided by a k-wire or the like. The inner shaft 68 may be configured to rotate with respect to the outer shaft 66. The inner shaft 68 may terminate at a distal tip 64. The distal tip 64 may have a hexalobular portion, for example, which engages with a portion of the screw mount 40. The distal tip 64 may be of any suitable shape and configuration including, but not limited to, round, triangular, squared, polygonal, star, torx, irregular, uniform, non-uniform, offset, staggered and/or tapered. The outer shaft 66 may also include a track portion 62 extending longitudinally along a length of the driver 60. The track portion 62 may be in the form of one or more extensions or recesses configured to mate with a corresponding track 46 on the screw mount 40.

Figure 2A:
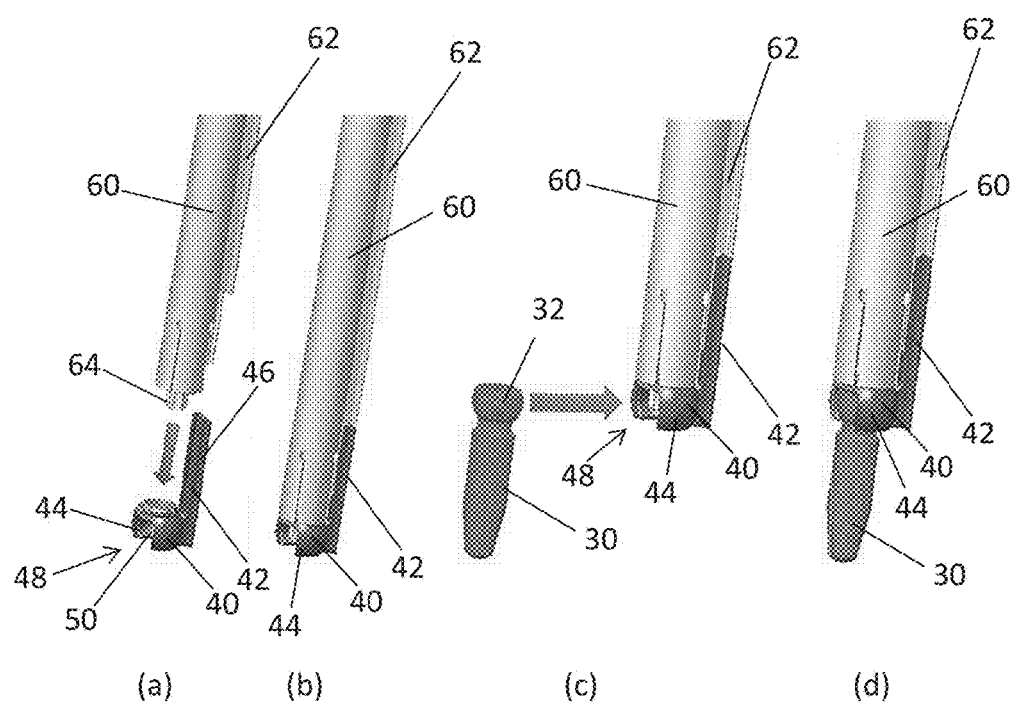
FIGS. 2A-2D illustrate the components and a series of steps, which may be used to install a pedicle screw in bone and mount a retractor blade thereto intra-operatively.

A series of steps, which may be used to install the pedicle screw 30 in bone and mount a retractor blade 20 thereto is further described. Any of these steps may be performed before or during the operation in any suitable order. The screw mounts 40 may be available as a kit or set, for example, in a caddy sitting upright (not shown), such that a user can use driver 60 to select a screw mount 40. With reference on FIG. 2A, shown in step (a), the driver 60 may be pressed downward onto the screw mount 40. In particular, the distal tip 64 of the driver 60 may include an extension configured to engage a corresponding recess in the top of the head portion 44 of the screw mount 40 and/or a recess in the head 32 of the screw member 30, for example, via a press-fit connection. In addition, the track portion 62 on the driver 60 may slidably engage the track 46 on the extension portion 42 of the screw mount 40. The corresponding and intermeshing tracks 46, 62 and press-fit connection of the tip 64 with head portion 44 may provide for visual, audible, and/or tactile feel when the driver 60 snaps onto the screw mount 40. The fully seated screw mount 40 on driver 60 is shown in step (b). After verifying the connection, a thumb knob (not shown) on the driver 60 can be utilized to make sure that the internal sphere 50 of the screw mount 40 is in the unlocked position (e.g., with apertures aligned to allow for side loading of the screw member 30).

As shown in step (c), the screw member 30 may be side-loaded into the screw mount 40. The hexalobular portion of the inner shaft 68 of the driver 60 may be pulled back and the screw head 32 inserted into the head portion 44 of the screw mount 40 from the side. The resulting construct is shown in step (d) with the screw member 30 received in screw mount 40 and attached to driver 60. The hexalobular portion of the driver 60 may then be pushed forward and engaged with the screw 30 (not visible).

Figure 2B:
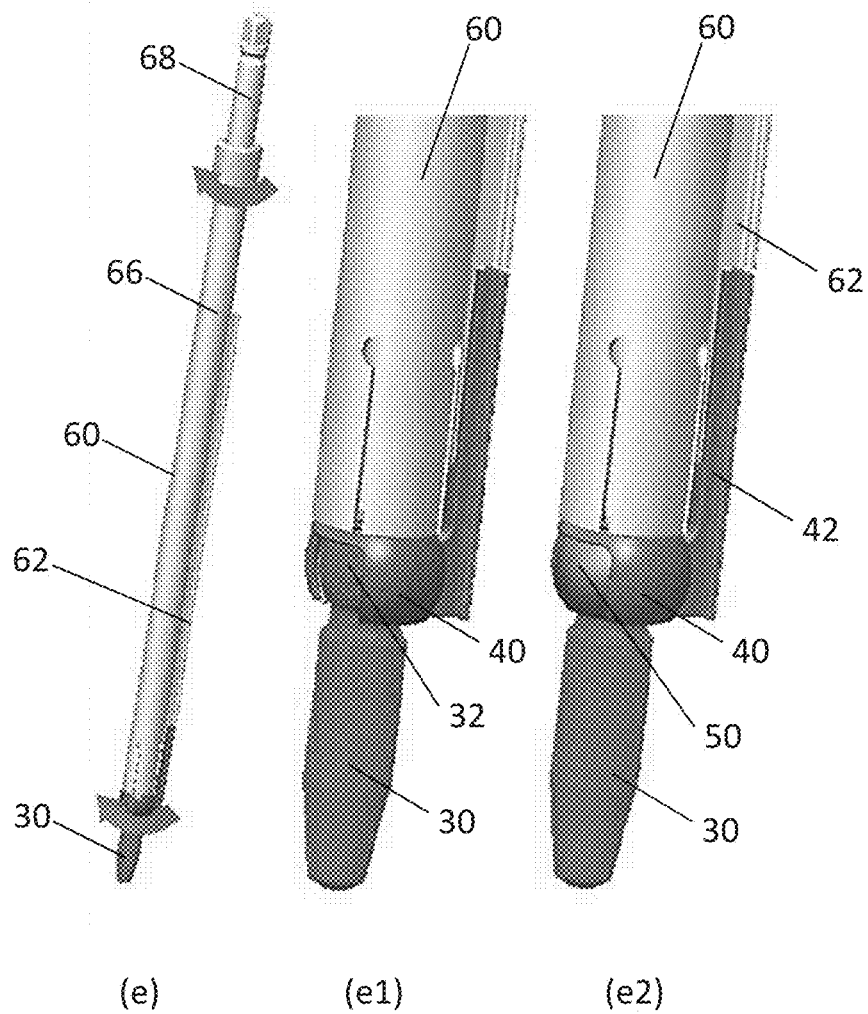

Turning now to FIG. 2B, as shown in step (e), the internal sphere 50 in the head portion 44 of the screw mount 40 may be rotated into the locked position. For example, a driver thumb knob may be rotated, for example, 180 degrees, to turn the internal sphere 50 to the locked position. A close up view of the screw mount 40 in the unlocked positioned is shown in (e1) and (e2) shows a close up view of the screw mount 40 in the locked position. A solid stop (not shown) may also be present to ensure that the internal sphere 50 remains in the locked position.

At the surgical site, a Jamshidi needle and k-wire may be placed into the pedicle. A series of cannulas may be inserted over the k-wire to dilate the tissue and obtain the blade length. The cannulas may then be removed, leaving the k-wire in place. The driver assembly, including the screw member 30 and screw mount 40 connected to the driver 60, may pass over the k-wire and the screw member 30 may be inserted into the pedicle (e.g., threaded into the pedicle).

Figure 2C:
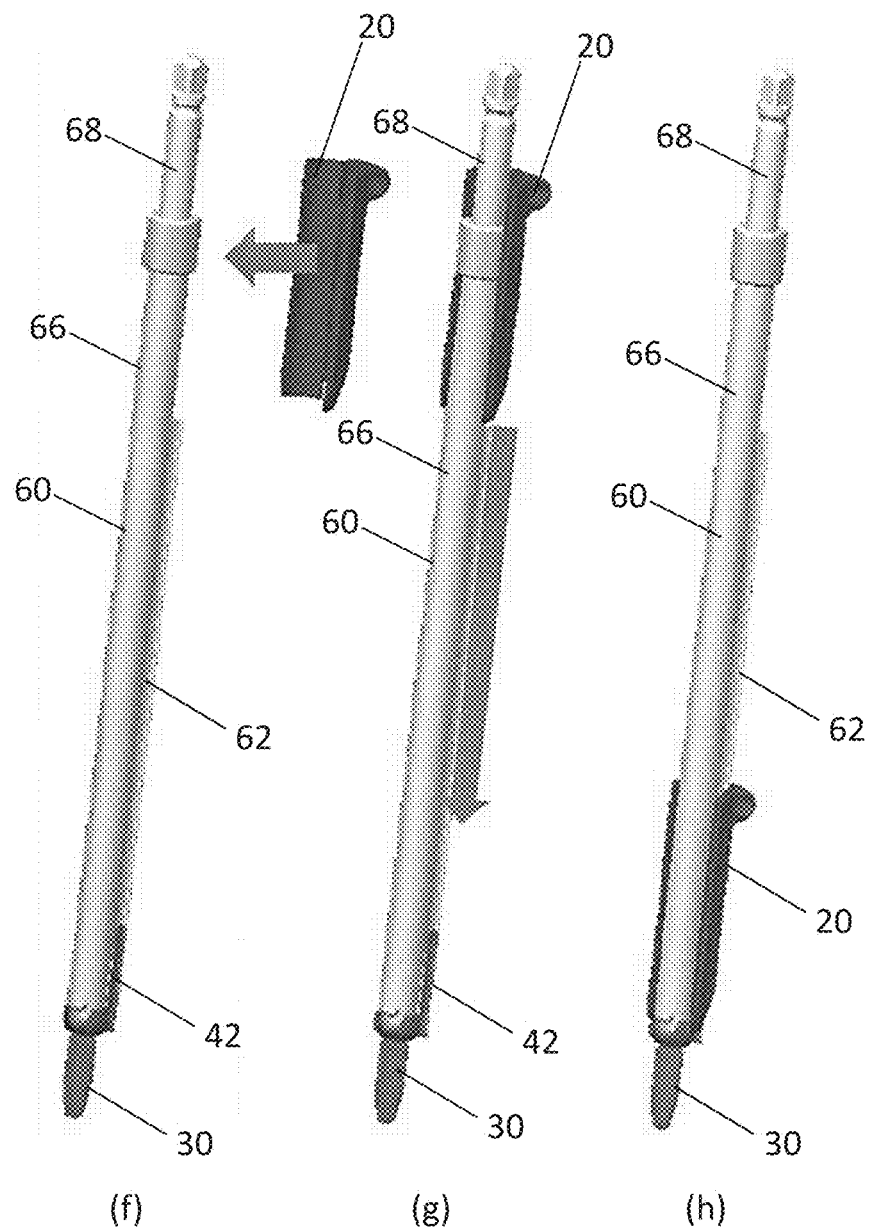

Turning now to FIG. 2C, prior to disconnecting the driver 60 from the screw mount 40, as shown in steps (f) and (g), the blade 20 may be engaged with the driver 60. As shown in step (h), the blade 20 may be slid down the side of the driver 60 and onto the screw mount 40. In particular, the blade 20 may also include a track configured to engage with the track 62 on the outer shaft 66 of the driver and connect with an outer portion of the extension portion 42 of the screw mount 40.

Figure 2D:
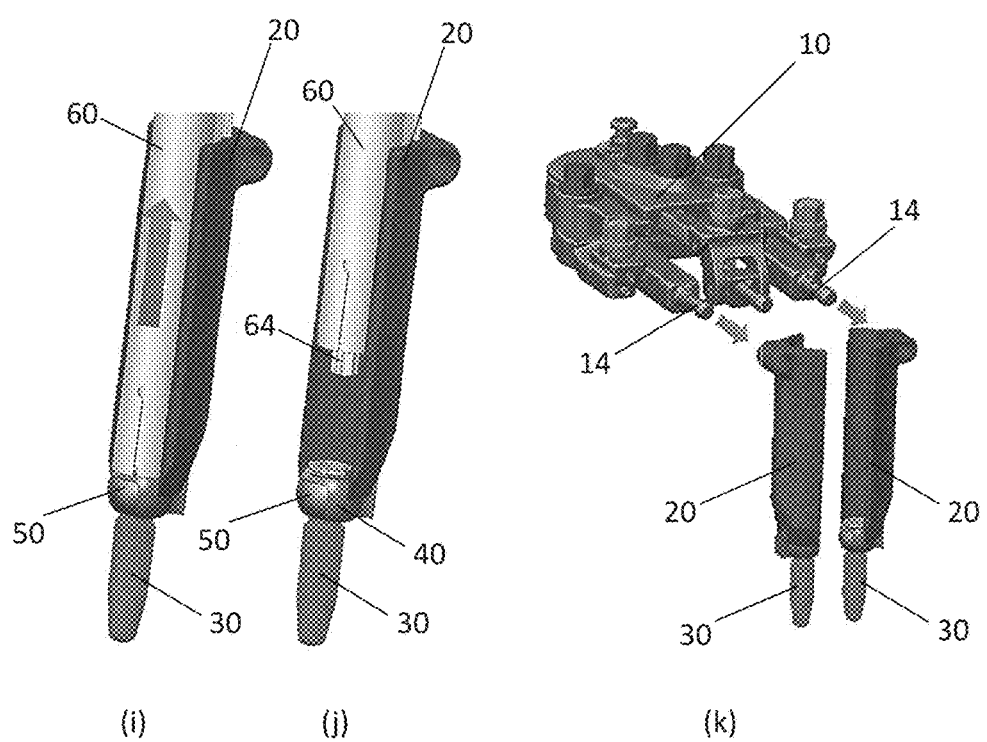

As best seen in FIG. 2D, in steps (i) and (j), once the blade 20 has been connected with the screw mount 40, the driver 60 can be removed. The series of driver assembly, screw insertion, blade insertion and driver removal may be repeated at the other pedicle sites as many times as necessary for the operation. Once the screws 30, screw mounts 40, and blades 20 are in place, as shown in step (k), the retractor body 10 can be attached to the blades 20, for example, from a side approach. As shown, the posts 14 can be positioned within openings in the blades 20. The blades 20, including the screw mounts 40 and screws 30, and the vertebral bodies attached thereto can now be manipulated by the retractor 10. For multi-level constructs, the retractor base 10 can be removed from the blades 20 and the retractor 10 reattached to adjacent blades 20. If necessary, the blades 20 and/or screw mount 40 may be rotated about the pedicle screw member 30 before the retractor 10 is reattached to adjacent blades 20.

After the interbody work has been completed, the same or a separate driver 60 may be introduced to turn the internal sphere 50 into the unlocked position. The retractor blades 20 can be retracted out further, thereby separating the screw member 30 from the screw mounts 40. The pedicle screws 30 can remain in the pedicles and can be used for a resulting fusion procedure (e.g., combined with rods). By moving the retractor blades 20 outward, this will allow enough space for screw tulips to be introduced and connected to the screw members 30. After rods and locking caps have been introduced, the retractor 10, blades 20, and screw mounts 40 may be removed, for example, at the same time.

Figures 3D, 3E:
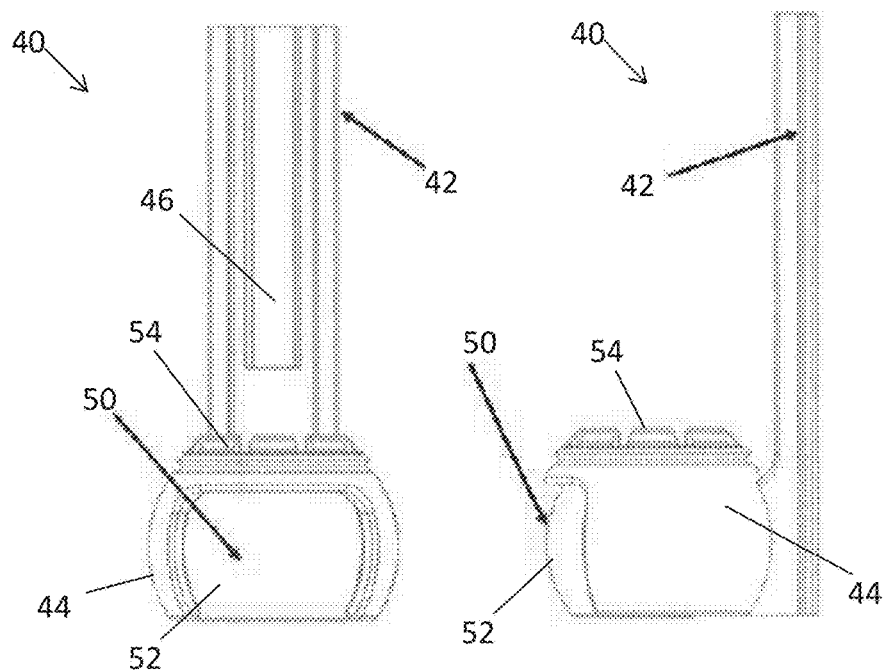
FIGS. 3A-3P provide addition detail on shims or screw mounts suitable for use in attaching a pedicle screw to the retractor blade.
Figure 3F:
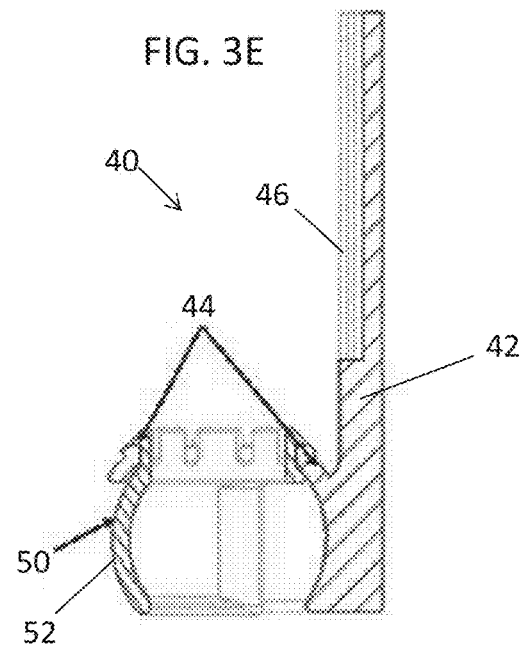
Figures 3G, 3H:
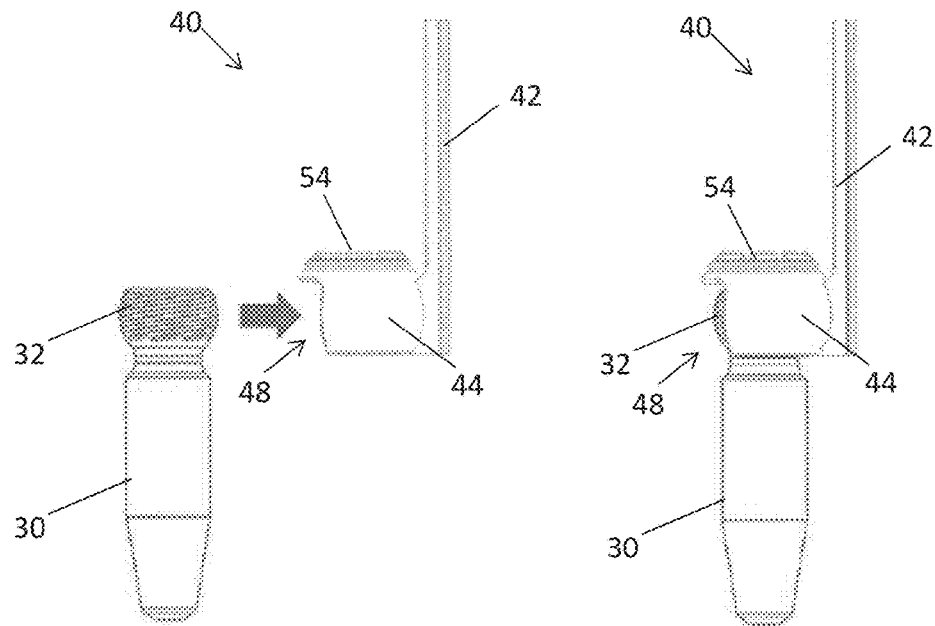
Figures 3I, 3J:
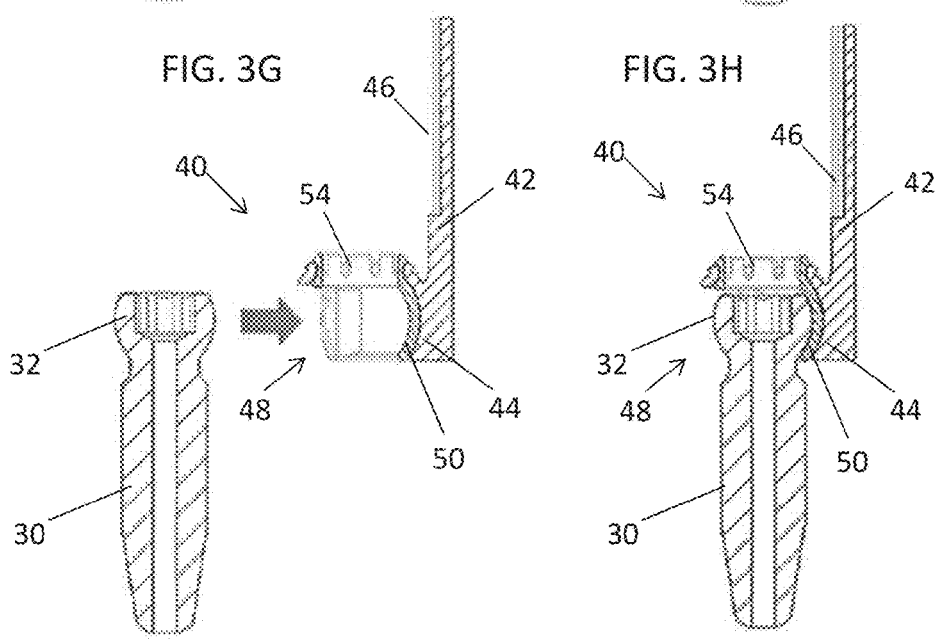
Figures 3K, 3L, 3M:
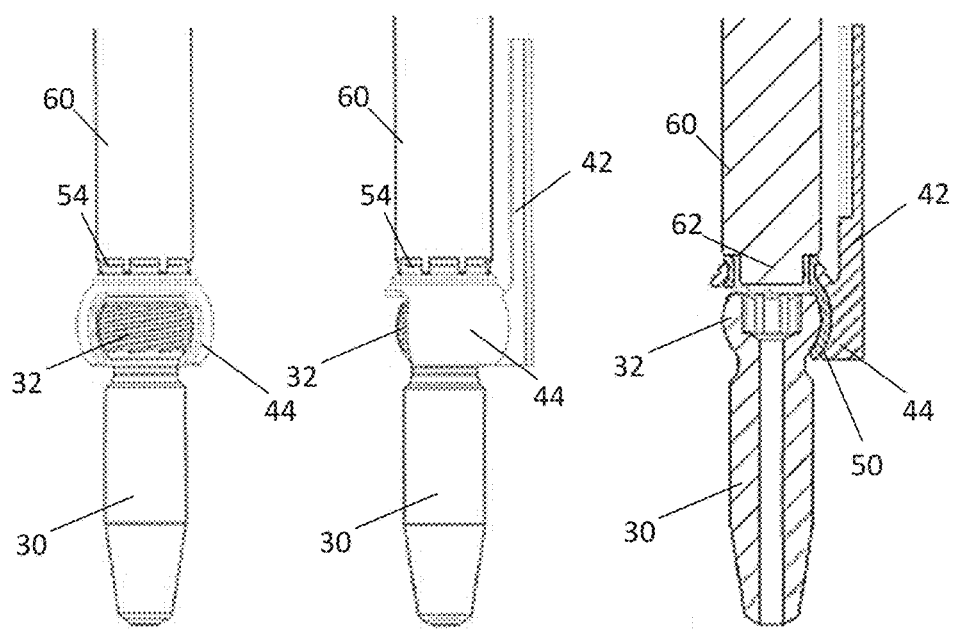
Figures 3N, 3O, 3P:
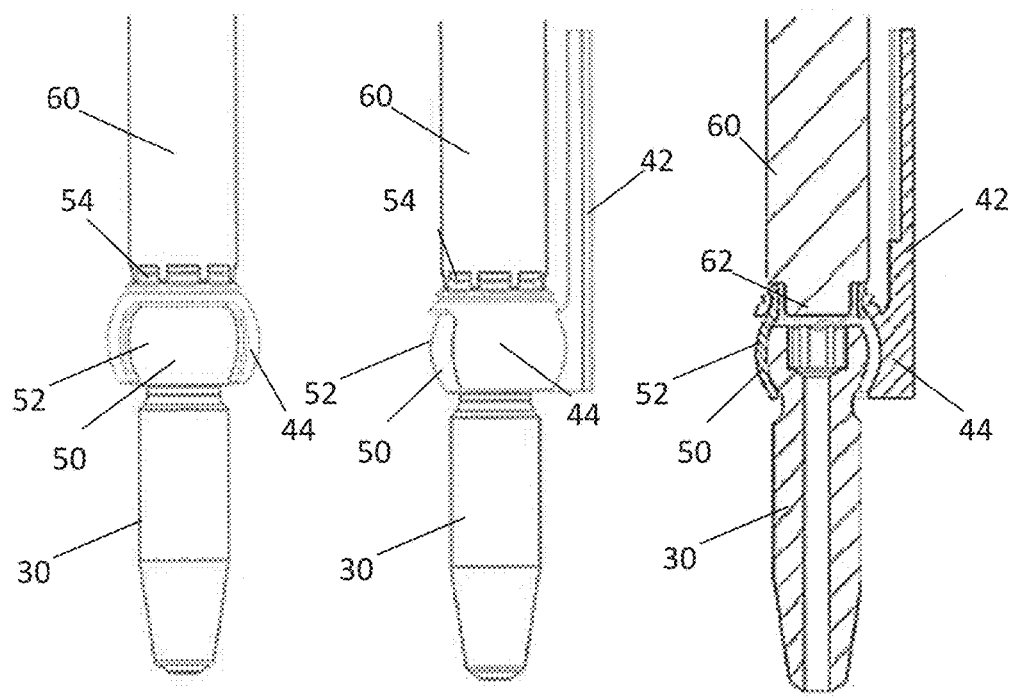

FIGS. 3A-3P provide further details of shim or screw mount 40, which may be used to connect blade 20 to screw 30, for example. The shim or screw mount 40 may include extension portion 42 and connection portion or head portion 44. The extension portion 42 may be in the form of an elongated member extending from a proximal end to a distal end. The extension portion 42 may include track 46 along a front surface. The track 46 may include one or more recesses or grooves extending along a longitudinal length of the extension portion 42. The track 46 is configured to engage and mate with a corresponding track portion 62 on driver 60.

The connection portion or head portion 44 of the screw mount 40 may be in the form of an outer spherical portion. The outer spherical portion of the head portion 44 may be generally rounded or spherical in shape and may be generally hollow within. The head portion 44 is preferably sized and shaped to receive at least a portion of the head 32 of screw member 30 therein. The head portion 44 preferably defines opening or aperture 48 in order to provide for side-loading of the screw member 30. The bottom of the head portion 44 also includes an opening configured to receive a portion of the shaft of the screw 30. The head portion 44 may be connected to the extension portion 42 at a distal end of the extension portion 42.

The head portion 44 preferably retains internal sphere 50 within. The internal sphere 50 may be sized and shaped to be retained within the head portion 44 of the screw mount 40. The internal sphere 50 also includes an opening configured to receive a portion of the shaft of the screw 30. The internal sphere 50 is preferably configured to rotate with respect to the head portion 44 of the screw mount 40. Internal sphere 50 may extend through an opening in the top of the head portion 44 such that the internal sphere is able to engage with driver 60. The internal sphere 50 may have an opening or aperture corresponding to aperture 48 in the head portion 44. FIGS. 3A-3C show an unlocked position of the internal sphere 50 such that the side-opening in the internal sphere 50 is aligned with the side-opening in the head portion 40. When unlocked, the screw member 30 may be side loaded into the screw mount 40.

FIGS. 3D-F depict screw mount 40 in a locked position (with the screw 30 absent). In other words, the internal sphere 50 is rotated, for example, by driver 60, such that the aperture 48 of the head portion 44 is substantially blocked by side wall 52 of the internal sphere 50, thereby locking the screw member 30 within the head portion 44 of the screw mount 40 in the locked position.

In one embodiment, only the inner sphere 50 is able to rotate. In an alternative embodiment, the two spherical members 44, 50 are each able to rotate independently of one another. Once the screw 30 is inserted into the internal sphere 50, the internal sphere 50 is rotated, for example, 180 degrees, to block the screw head 32 from being removed from the direction that it was inserted. The external sphere 44 contains the screw 30 from being removed from the back side. A physical stop may be provided to give the surgeon feedback to know when the internal sphere 50 has been rotated to the locked position. A feature 54 on the top of the internal sphere 50 may be utilized to allow the driver 60 to mate with the sphere 50 and turn it. The feature 54 may include one or more recesses and/or protrusion, for example, having a round, triangular, squared, polygonal, star, torx, irregular, uniform, non-uniform, offset, staggered and/or tapered shape configured to engage with the distal tip 64 of the driver 60. The outer sphere 44 is retained by the retractor blade 20 to keep it from spinning with the inner sphere 50. The screw 30 can retain its ability to rotate and pivot to a desired angle. The internal sphere 50 can be rotated, for example another 180 degrees, to unblock the screw 30 for removal from the screw mount 40.

As shown in FIGS. 3G-3P, the steps for inserting screw 30 are shown for side-loading the screw 30 into the mount 40. In FIGS. 3G and 3I, the head 32 of the screw 30 is aligned with the opening 48 in the outer sphere 44. The inner sphere 50 is in the unlocked position. In FIGS. 3H and 3J, the head 32 of the screw is inserted in the inner sphere 50 that is positioned inside the outer sphere 44. FIGS. 3K-3M show driver 60 engaging the top of inner sphere 50. FIGS. 3N-3P show the inner sphere 50 rotated to the locked position such that the side wall 52 of the inner sphere 50 blocks the aperture 48 of the outer sphere 44.

Turning now to FIGS. 4A-4C, another mechanism of attachment between the retractor blade 120 and the pedicle screw 130 is shown. In particular, FIG. 4A depicts a front view of the blade assembly 100 including screw mount or shim 140 connecting the pedicle screw 130 to the retractor blade 120. In this design, the screw mount or shim 140 wraps around the outer edges of the blade 120 to keep it in place. FIG. 4B depicts a side view of an edge 142 of the shim 140 engaged with the blade 120. The blade 120 extends from a proximal end portion 122 to a distal end portion 124 configured to engage with and retract soft tissues and/or muscle. The blade 120 has a generally curved inner portion configure to mate with a generally curved portion of the shim 140. The blade 120 includes two extensions or end portions 118 at the outer most portions of the curved blade. These end portions 118 may extend along a portion or an entire length of the blade 120 from the proximal end 122 to the distal end 124. The shim 114 includes extension portions with edges 142 configured to surround the end portions 118 of the blade 120. FIG. 4C shows a top view of the assembly 100.

When installing the assembly 100 or a portion thereof, the bone screw 130 may be threaded in to the pedicle and the screw mount 140 may be added before or after the bone screw 130 is engaged with the pedicle. With the bone screw 130 and shim 140 in place, the retractor blade 120 slides into the shim 140. One or more locks 126 (e.g., two locks 126 shown in FIG. 4A) may be provided on the outer edges or end portions 118 of the blade 120 such that the locks 126 engage once the screw 130 is fully engaged inside the bone. One or more stops 128 (e.g., two stops 128 shown in FIG. 4A) may also be provided on the blade 120 at the distal end 124 to prevent the shim 140 from backing out proximally during the surgery. A removal slot and/or tab 152 may be operable by a removal tool to disengage the distal end of the shim 140 from the head of the screw 130, thereby allowing the shim 140 to slide back up the outer edges of the blade 120 and separate from the blade 120.

Figure 5A:
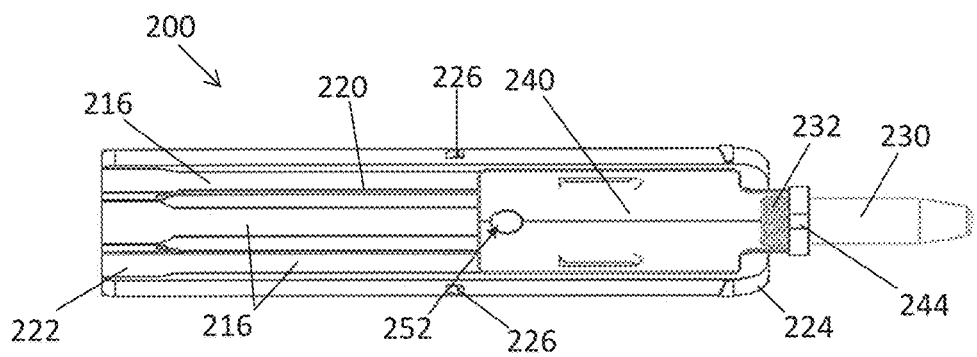
FIGS. 5A-5C show attachment of a retractor blade member to a pedicle screw according to yet another embodiment.
Figure 5B:
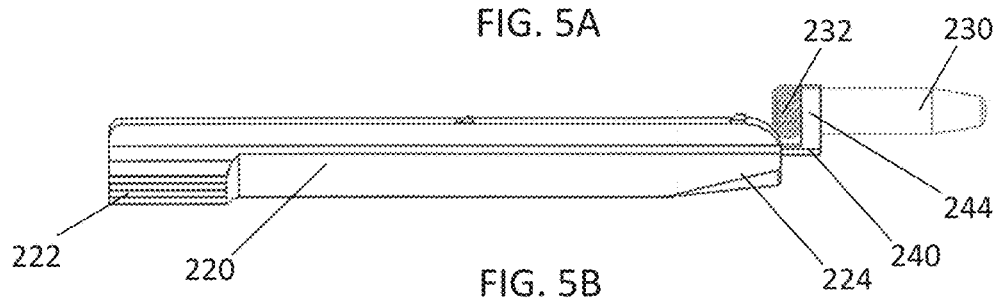
Figure 5C:
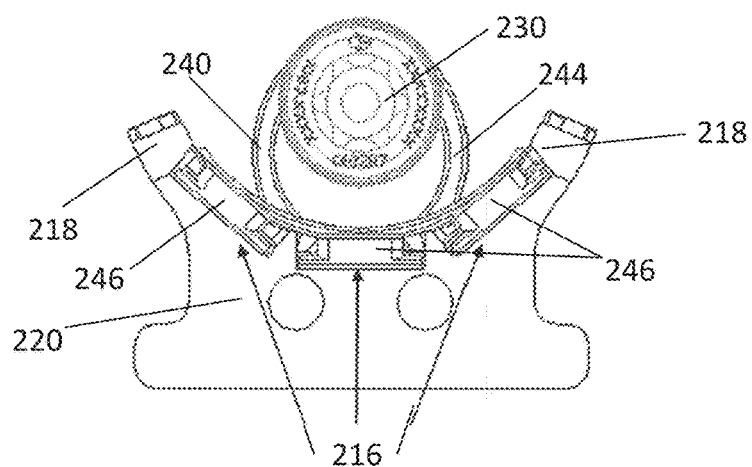

FIGS. 5A-5C depict an alternative version of a blade assembly 200 where the screw mount or shim 240 engages interior rails 216 on the blade 220. In FIG. 5A, a front view of the blade assembly 200 is shown including screw mount or shim 240 connecting the pedicle screw 230 to the retractor blade 220. In this design, the shim 240 slides down the interior rails 216 of the blade 220 to keep the shim 240 in place. FIG. 5B depicts a side view of the shim 240 engaged with the blade 220. The blade 220 extends from a proximal end portion 222 to a distal end portion 224 configured to engage with and retract soft tissues. In one embodiment, the blade 220 is identical to blade 120 such that shim 240 and shim 140 are interchangeable with the same blade 120, 220 design. One or more locks 226 (e.g., two locks 226 shown in FIG. 5A) may be provided on the outer edges or end portions of the blade 220, for example, if shim 140 where selected.

The blade 220 may have a generally curved inner portion having one or more rails 216, for example, in the form of channels or grooves, defined along a portion or an entire length of the blade 220 from the proximal end 222 to the distal end 224. The shim 214 includes corresponding rails 246, for example, in the form of ridges or tongues, configured to be received within and slidably engage the rails 216 of the blade 220. FIG. 5C shows a top view of the assembly 200. The shim 214 also includes a partial or complete ring 244 configured to at least partially surround or rest below the head portion 242 of the screw 230. As the bone screw 230 is driven into the pedicle, one or more dimples may be centered inside the rails 216 (e.g., the outer two rails 216) of the blade 220 that engage with the shim 240 while the screw 230 is being driven into the bone. A removal tool can be used to allow the shim 240 to slide back up the rails 216 and separate from the blade 220.

Figures 6A, 6B, 6C, 6D:
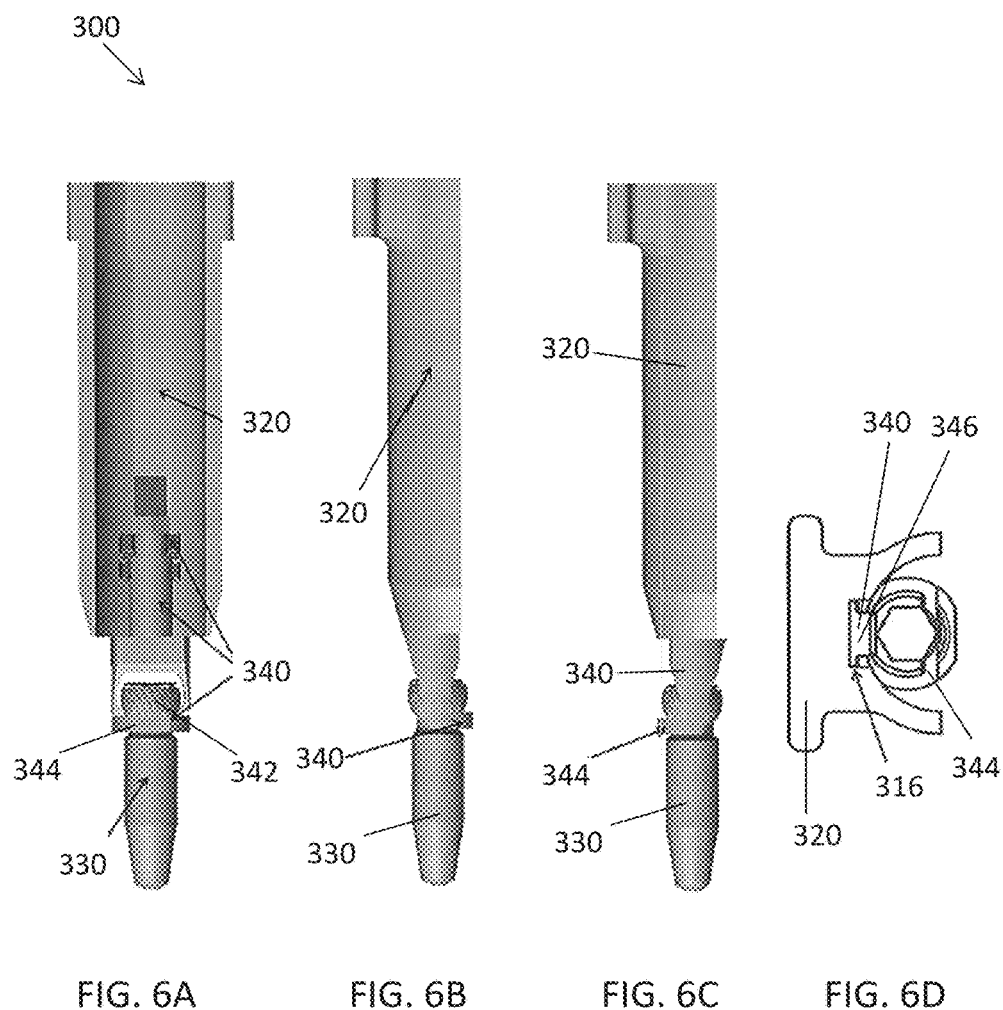
FIGS. 6A-6D depict an alternative attachment mechanism between a pedicle screw and a retractor blade.

Turning now to FIGS. 6A-6D, another mechanism of attachment between the retractor blade 220 and the pedicle screw 330 is shown. In particular, FIG. 6A depicts a front view of the blade assembly 300 including screw mount or rotating shim 340 connecting the pedicle screw 330 to the retractor blade 320. In this design, the shim 340 is configured to rotate or spin in order to catch and lock or unlock the pedicle screw 330 to the blade 220.

The blade 220 may have a generally curved inner portion having one or more rails 316, for example, in the form of channels or grooves, defined along a portion or an entire length of the blade 320. Similar to assembly 200, the shim 340 may be configured to slide down the interior rail 316 of the blade 320 to keep the shim 340 in place. In this case, the rail 316 may be a single, central rail 316 in the form of an internal T-slot, for example. The shim 314 includes a corresponding rail 346, for example, in the form of a ridge or tongue, configured to be received within and slidably engage the rail 316 of the blade 320. In particular, the shim 314 may include a single, central T-rail 346. FIG. 6D shows a top view of the assembly 300. The shim 314 also includes a partial ring 344 configured to at least partially surround or rest beneath the head portion 342 of the screw 330. The ring 344 includes an opening to allow for side loading of the screw 330 onto the shim 340.

The pedicle screw 330 may be inserted into the pedicle, for example, using an open or MIS approach. The rotating shim 340 may be inserted into the retractor blade 320 via the internal T-slot 316 and T-rail 346. The rotating shim 340 can be locked in place using one or more dimples, for example. With the shim 340 inserted, the retractor blade 320 and shim 340 can be inserted into the incision and moved (e.g., cephalad and/or caudal) until the shim 340 hooks onto the pedicle screw 330. The shim 340 may or may not lock to the screw 330. Once attached for all pedicles, the blades 320 may be attached to the retractor body. To disconnect the shim 340 from the screw 330, a tool (e.g., a hex tool) may be configured to rotate the shim 340 (e.g., 180°) while still in the blade 320, thereby allowing for the blades to be retracted further (e.g., cephalad and/or caudal) without being attached to the pedicle screws 330 any further.

FIGS. 7A-7C depict assembly 400 including retractor blade 420, shim 440, and pedicle screw 430. In this embodiment, the shim 440 is in the form of a split collet. For example, the shim 440 may include two separate arms separated by a longitudinal slot having a ring 444 at a distal-most end. A slight interference between the collet 440 and screw head 432 allows the shim 440 to be clicked over the shank of the screw 430. The shim 440 may snap over the screw head 432 and be inserted through the incision with the pedicle screw 430. Once the screw 430 is in place, the retractor blade 420 may be inserted and slid over the shim 440 using an internal T-slot similar to that described in assembly 300. There may be no secondary locking between the screw 430 and the shim 440 and retractor blade 420. Alternatively, there may be an extended groove or slot 448 for addition tightening. As best seen in FIG. 7B, as the retractor blades 420 slides down, there is an elongated slot 448 in the shim interference causing the collet 440 to tighten further, thereby better locking screw 430 to the shim 440. With the blades 420 connected to the shims 440 and screws 420, the retractor can be attached to the retractor blades 420. To remove the shim 440, a separate tool can be used to loosen the connection between the shims 440 and the screw 430 to remove the shim 440 from the retractor blade 420.

FIGS. 8A-8C illustrate an alternative embodiment for attachment between the pedicle screw 530 and the blade 520. In this embodiment, the screw 530 is directly attached to the blade 520 using a wire, filament, fiber, or cable 540. The cable 540 may include any suitable elongate element configured to engage the pedicle screw and the blade 520 at one or more points of contact. For example, the retractor blade 520 may have the cable 540 attached on one end, for example, at the top of the blade 520. The cable 540 may be routed down the blade tip where it will form a hoop and be routed back up to the top of the blade 520. The cable 540 may extend through one or more openings in the blade 520, for example. The shank of the screw 530 may be threaded into the pedicle using a driver, for example. Prior to removing the driver, a slackened hoop of cable 540 may be placed around the driver and the blade 520 may be inserted down the incision using the driver as a guide. Once the retractor blade 520 reaches its predetermined depth, the cable 540 can be tightened, for example, using one or more thumb knobs 550, thereby taking up the slack and tightening the cable 540 around the screw 530. Thumb knobs 550 may be in the form of wheels or cylinders, for example, attached to the proximal end of the blade 520. The thumb knobs 550 may be configured to rotate such that the cable 540 winds around the base of the knobs 550. The driver can then be detached and removed from the incision. If needed, distraction of the disc space can take place, for example, using the pedicle screws 530. To remove the retractor blade 520 from the screw 530 after the retraction is no longer needed, the cable 540 can be slacked again or disconnected entirely from one or both ends. As the blades 520 are removed, the cable 540 can unwind and pull free from the screw 530.

Components of all of the devices disclosed herein can be made of materials known to those skilled in the art, including metals (e.g., titanium), metal alloys (e.g., stainless steel, cobalt-chromium, and titanium alloys), ceramics, polymers (e.g., polyether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. In some embodiments, the devices may include radiolucent and/or radiopaque materials. The components can also be machined and/or manufactured using techniques known to those skilled in the art.

Advantageously, the blades, retractor systems, and associated devices described herein can be used with a number of different implants and devices. For example, the retractor systems and devices can be used to provide access to a surgical site such that a device that preserves motion can be provided. In addition, the retractor systems and devices can be used to provide access to a surgical site such that a fusion device, such as a cage or spacer, or standalone device, can be provided. In addition, the retractor systems and devices can be used to provide access to various other devices, including but not limited to rods, screws (e.g., pedicle screws, cortical screws, etc.), plates and various other implants that are used in spine surgery.

As described herein, the specially designed connections between the pedicle screw and retractor blade provide for improved pedicle-based retraction and distraction. The connections create a secure reversible connection between the pedicle screw and the retractor blade. The connections can be made before or during the operation, and if inserted intra-operatively, the blade may be attached to and removed from the screw in a manner to minimize the amount of tissue disruption at the surgical site.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A method of retracting and distracting a disc space between first and second vertebrae, the method comprising:
   providing a retractor assembly comprising:
      a retractor body;
      a first retractor blade having a proximal end configured to engage the retractor body and a distal end configured to retract soft tissue;

a first pedicle screw having a head portion removably connectable to the distal end of the first retractor blade and a shaft portion configured to engage bone; and a first shim having an extension portion, an outer spherical portion, and an inner spherical portion rotatably received within the outer spherical portion, wherein the extension portion is configured to engage the first retractor blade and the inner spherical portion is configured to receive the head portion of the first pedicle screw, wherein the inner spherical portion rotates from an unlocked position to a locked position for retaining the head portion of the first pedicle screw within the first shim; connecting a driver to the first shim;

attaching the first pedicle screw to the first shim by side loading the first pedicle screw into the first shim and locking the first pedicle screw to the first shim;

attaching the first pedicle screw to a pedicle of the first vertebra;

sliding the first retractor blade having a proximal portion and a distal portion down the driver and onto the first shim such that the distal portion of the first retractor blade connects to the first shim;

removing the driver; and connecting the retractor body to the proximal portion of the first retractor blade.

2. The method of claim 1 further comprising:
connecting the driver to a second shim;
attaching a second pedicle screw to the second shim by side loading the second pedicle screw into the second shim and locking the second pedicle screw to the second shim;
attaching the second pedicle screw to a pedicle of the second vertebra;
sliding a second retractor blade having a proximal portion and a distal portion down the driver and onto the second shim such that the distal portion of the second retractor blade connects to the second shim;
removing the driver;
connecting the retractor body to the proximal portion of the second retractor blade; and
retracting and distracting the disc space using the first and second retractor blades and the first and second pedicle screws, respectively.

3. The method of claim 1, wherein the extension portion includes at least one rail configured to slidably engage at least one corresponding rail on the first retractor blade.

4. The method of claim 1, wherein the extension portion includes at least one edge configured to surround one or both end of the first retractor blade.

5. The method of claim 1, wherein the first retractor blade includes a generally curved inner portion having one or more grooves defined along at least a portion of the first retractor blade, the one or more grooves configured to slidably engage one or more corresponding tongues of the extension portion of the first shim.

6. The method of claim 1, wherein a top portion of the inner spherical portion extends through an opening in the outer spherical portion, and the top portion is configured to be engaged by the driver in order to rotate the inner spherical portion from the unlocked position to the locked position.

7. The method of claim 1, wherein the outer spherical portion and the inner spherical portion each include an opening that, when aligned, allow the first pedicle screw to be side-loaded into the shim.

8. The method of claim 1, wherein the first pedicle screw is configured to polyaxially rotate in the first shim.

9. The method of claim 1, wherein the driver includes at least one track configured to engage at least one rail on the extension portion of the first shim.

10. A method of retracting and distracting a disc space between first and second vertebrae, the method comprising:
providing a retractor blade assembly comprising:
a retractor blade having a proximal end configured to engage a retractor body and a distal end configured to retract soft tissue;
a screw having a head portion removably connectable to the distal end of the retractor blade and a shaft portion configured to engage bone; and
a shim having an extension portion and a connection portion, wherein the extension portion is configured to engage the retractor blade and the connection portion is configured to receive at least a portion of the screw, wherein the connection portion is movable from an unlocked position to a locked position for retaining the screw within the shim,
wherein the connection portion includes an outer spherical portion and an inner spherical portion, a top portion of the inner spherical portion extends through an opening in the outer spherical portion, and the top portion is configured to be engaged by a driver in order to rotate the inner spherical portion from the unlocked position to the locked position attaching the screw to the shim by side loading the screw into the shim and locking the screw to the shim;

attaching the screw to a pedicle of the first vertebra;

sliding the retractor blade having a proximal portion and a distal portion down the driver and onto the shim such that the distal portion of the first retractor blade connects to the shim;

removing the driver; and connecting a retractor body to the proximal portion of the retractor blade.

11. The method of claim 10, wherein the extension portion includes at least one rail configured to slidably engage at least one corresponding rail on the retractor blade.

12. The method of claim 10, wherein the extension portion includes at least one edge configured to surround one or both end portions of the retractor blade.

13. The method of claim 10, wherein the retractor blade includes a generally curved inner portion having one or more grooves defined along at least a portion of the retractor blade, the one or more grooves configured to slidably engage one or more corresponding tongues of the extension portion of the shim.

14. The method of claim 10, wherein the connection portion is configured to rotate relative to the retractor blade.

15. The method of claim 10, wherein the shim includes an elongated slot extending longitudinally along a length of the shim.

16. The method of claim 10, wherein the connection portion includes at least a partial ring configured to at least partially surround the head portion of the screw.

17. The method of claim 10, wherein one or more locks are positioned along one or both outer edges of the retractor blade to prevent the shim from sliding off the retractor blade.

* * * * *